(12) United States Patent
Norioka et al.

(10) Patent No.: US 7,579,165 B2
(45) Date of Patent: Aug. 25, 2009

(54) METHODS FOR DERIVATIZING PROTEIN OR PEPTIDE WITH SULFONIC ACID GROUPS

(75) Inventors: Shigemi Norioka, Ibaraki (JP); Minoru Yamaguchi, Kyoto (JP); Hiroki Kuyama, Kyoto (JP); Takashi Obama, Kyoto (JP); Eiji Ando, Kyoto (JP); Takashi Nakazawa, Nara (JP); Norikazu Ueyama, Osaka (JP); Taka-aki Okamura, Osaka (JP)

(73) Assignee: Shimadzu Corporation, Kyoto (JP)

( * ) Notice: Subject to any disclaimer, the term of this patent is extended or adjusted under 35 U.S.C. 154(b) by 196 days.

(21) Appl. No.: 10/962,575

(22) Filed: Oct. 13, 2004

(65) Prior Publication Data

US 2005/0084927 A1    Apr. 21, 2005

(30) Foreign Application Priority Data

Oct. 16, 2003   (JP) .............................. 2003-356809

(51) Int. Cl.
| | |
|---|---|
| C07K 1/13 | (2006.01) |
| C07K 1/14 | (2006.01) |
| C07K 14/00 | (2006.01) |
| C12P 21/06 | (2006.01) |
| C12Q 1/00 | (2006.01) |
| C12Q 1/34 | (2006.01) |
| C12Q 1/37 | (2006.01) |
| G01N 33/53 | (2006.01) |
| G01N 33/38 | (2006.01) |
| G01N 33/483 | (2006.01) |

(52) U.S. Cl. ........................ 435/68.1; 435/7.5; 435/18; 435/23; 435/24; 530/300; 530/324; 530/325; 530/326; 530/327; 530/328; 530/329; 530/406

(58) Field of Classification Search ....................... None
See application file for complete search history.

(56) References Cited

U.S. PATENT DOCUMENTS 6,156,527 A * 12/2000 Schmidt et al. ............... 435/24
2005/0042676 A1  2/2005 Hamon et al.

OTHER PUBLICATIONS

Keough et al., "A Method for High-Sensitivity Peptide Sequencing Using Postsource Decay Matrix-Assisted Laser Desorption Ionization Mass Spectrometry", Proceedings of the National Academy of Science of the United States of America, Vo.l 96, pp. 7131-7136, Jun. 1999.*

Schnaar et al., "Reversible Covalent Immobilization of Ligands and Proteins on Polyacrylamide Gels", Analytical Biochemistry, Vo.l 151, pp. 268-281, 1985.*

Burlet et al., "Influence of Cysteine to Cysteic Acid Oxidation on the Collision-Activated Decomposition of Protonated Peptides: Evidence for Intraionic Interactions", vol. 3, pp. 337-344, 1992.*

Hellman et al., "Easy Amino Acid Sequencing of Sulphonated Peptides Using Post-Source Decay on a Matrix-Assisted Laser Desorption/Ionization Time-of-Flight Mass Spectrometer Equipped With a Variable Voltage Reflector", Rapid Commun. Mass Spectrom., vol. 16, pp. 1851-1859, 2002.*

Nilsson J, Larsson M, Stahl S, Nygren P-A, Uhlen M, Multiple Affinity Domians for the Detection, Purification and Immobilizationof Recombinant Proteins, Journal of Molecular Recognition, 1996, 9: 585-594.*

T. Keough et al., "A Method for High-Sensitivity Peptide Sequencing Using Postsource Decay Matrix-Assisted Laser Desorption Ionization Mass Spectrometry", Proceeding of the National Academy of Science of the United States of America, vol. 96, pp. 7131-7136, Jun. 1999.

\* cited by examiner

*Primary Examiner*—Cecilia Tsang
*Assistant Examiner*—Julie Ha
(74) *Attorney, Agent, or Firm*—Cheng Law Group PLLC

(57) ABSTRACT

The present invention provides a method for effectively introducing sulfonic acid groups into the N-terminus of a protein or a peptide. The method comprises a modification step to react a N-terminus in a protein or peptide with a compound A which includes disulfide group and a cleavage step to cleave a disulfide bond of the disulfide group to convert into a sulfonic acid group. The present invention also provides a method of analyzing proteins or peptides easily and effectively on mass spectrometry and an intermediate that can be used to effectively derivatize proteins or peptides as sulfonic acid derivatives.

17 Claims, 4 Drawing Sheets

SEQUENCE LISTING

```
<160> NUMBER OF SEQ ID NOS: 2

<210> SEQ ID NO 1
<211> LENGTH: 5
<212> TYPE: PRT
<213> ORGANISM: Artificial Sequence
<220> FEATURE:
```

-continued

```
<221> NAME/KEY: BINDING
<222> LOCATION: (1)
<223> OTHER INFORMATION: AMIDATION
<220> FEATURE:
<223> OTHER INFORMATION: Description of Artificial Sequence: amidated
      peptide having sequence of metastasis-inhibiting active site in
      laminin

<400> SEQUENCE: 1

Tyr Ile Gly Ser Arg
 1               5

<210> SEQ ID NO 2
<211> LENGTH: 5
<212> TYPE: PRT
<213> ORGANISM: Artificial Sequence
<220> FEATURE:
<221> NAME/KEY: BINDING
<222> LOCATION: (1)
<223> OTHER INFORMATION: GUANIDINATION
<220> FEATURE:
<221> NAME/KEY: BINDING
<222> LOCATION: (1)
<223> OTHER INFORMATION: SUBSTITUTION by the group
      Bio-NH(CH2)2-SS-(CH2)2-CO, wherein Bio represents a biotinyl group
<220> FEATURE:
<223> OTHER INFORMATION: Description of Artificial Sequence: a part of
      Lysozyme with guanidinated at lysine and modified at the
      N-terminus.

<400> SEQUENCE: 2

Lys Val Phe Gly Arg
 1               5
```

METHODS FOR DERIVATIZING PROTEIN OR PEPTIDE WITH SULFONIC ACID GROUPS

BACKGROUND OF THE INVENTION

1. Field of the Invention

The present invention relates to the field of mass spectrometry for determining the amino acid sequence of proteins or peptides.

2. Disclosure of the Related Art

Some of the known processes for derivatization of proteins or peptides to sulfonic acid derivatives are carried out by directly reacting a sulfonic acid or a sulfonyl group-containing compound with the N-terminus of proteins or peptides. A drawback of this approach is that the reaction species have strongly acidic groups that affect the reaction efficiency at the N-terminus of proteins or peptides.

In one technique, reagents such as 2-sulfobenzoic acid cyclic anhydride and chlorosulfonylacetyl chloride are used to introduce sulfonic acid groups at the N-terminus of peptides (*Proc. Natl. Acad. Sci. USA* Vol. 96, pp. 7131-7136, June 1999).

It is not possible, however, to selectively collect the N-terminal fragments or selectively derivatize the N-terminal fragments to sulfonic acid derivatives by using the technique, since, according to this technique, the reagents are applied to tryptic peptides.

SUMMARY OF THE INVENTION

Accordingly, it is a first object of the present invention to provide a method for effectively introducing sulfonic acid groups into the N-terminus of a protein or a peptide to thereby derivatize the protein or the peptide as sulfonic acid derivative. In this objective, the method, which allows selective collection of the N-terminal fragments of a protein or a peptide as well as selective derivatization of N-terminal fragments with sulfonic acid groups; and is useful in the mass spectrometry analysis, is provided.

It is a second object of the present invention to provide a method capable of analyzing proteins or peptides easily and effectively on mass spectrometry. In this objective, the method, which is capable of analyzing proteins or peptides easily and effectively by collecting the N-termini of a protein or peptide as a sulfonic acid derivative to detect y-series ions on mass spectrometry, is provided.

It is a third object of the present invention to provide an intermediate that can be used to effectively derivatize proteins or peptides as sulfonic acid derivatives. In this objective, the intermediate which is useful in the selective collection and mass spectrometry of N-terminal fragments is provided.

1. The invention described in (1) through (18) below concerns a method for derivatizing proteins or peptides to sulfonic acid derivative:

Described in (1) below is an embodiment comprising a modification step using a compound A, and a cleavage step.

(1) A method for derivatizing a protein or peptide to a sulfonic acid derivative, comprising steps of:

modification step to react a N-terminus in a protein or peptide with a compound A which includes disulfide group, to obtain a protein or peptide modified with the compound A at the N-terminus; and cleavage step to cleave a disulfide bond of the disulfide group to convert into a sulfonic acid group, thereby converting the modified protein or peptide into a sulfonic acid derivative.

Described in (2) and (3) below is the structure of the compound A according to (1).

(2) The method according to above (1), wherein the compound A includes a functional group capable of reacting the N-terminus in the protein or peptide.

(3) The method according to above (2), wherein the functional group capable of reacting the N-terminus in the protein or peptide is selected from the group consisting of a carboxyl group, an isothiocyanate group, a succinimidyloxycarbonyl group, a p-nitrophenyloxycarbonyl group, a pentafluorophenyloxycarbonyl group, and a tetrafluorosulfophenyloxycarbonyl group.

Described in (4) and (5) below is the cleavage step according to (1).

(4) The method according to any one of above (1) to (3), wherein the conversion to the sulfonic acid group in the cleavage step is carried out by oxidatively cleaving the disulfide bond.

(5) The method according to any one of above (1) to (3), wherein the conversion to the sulfonic acid group in the cleavage step is carried out by reductively cleaving the disulfide bond and subsequently an oxidative reaction.

Described in (6) and (7) below is an embodiment according to (1) including a protection step before the modification step.

(6) The method according to any one of above (1) to (5), further comprising, before the modification step, a protection step to protect the side chain amino group of the protein or peptide.

(7) The method according to above (6), wherein in the protection step the side chain amino group is protected by guanidination.

Described in (8) below is an embodiment according to (1) including a fragmentation step and a separation step after the modification step and before the cleavage step.

(8) The method according to any one of above (1) to (7), further comprising, after the modification step and before the cleavage step, the steps of:

fragmentation step to fragmentize the protein or peptide modified with the compound A into one N-terminal peptide fragment derived from the N-terminus in the protein or peptide as well as modified with the compound A, and one or more of peptide fragments other than the N-terminal peptide fragment; and separation step to separate the N-terminal peptide fragment from the other peptide fragments to selectively collect the N-terminal peptide fragment, wherein in the cleavage step the disulfide bond in the N-terminal peptide fragment that originate from the compound A is cleaved to be converted into the sulfonic acid group and thereby the derivatized N-terminal peptide fragment is obtained.

Described in (9) and (10) below is an embodiment wherein the immobilized compound A is used.

(9) The method according to any one of above (1) to (8), wherein in the modification step firstly an immobilized compound A comprising the compound A further bound to a solid support is prepared; and subsequently the immobilized compound A is reacted with the N-terminus in the protein or peptide to obtain the protein or peptide modified with the immobilized compound A at the N-terminus.

(10) The method according to above (8), wherein
in the modification step firstly an immobilized compound. A comprising the compound A further bound to a solid support is prepared, and subsequently the immobilized compound A is reacted with the N-terminus in the protein or peptide to obtain the protein or peptide modified with the immobilized compound A at the N-terminus;
in the fragmentation step the N-terminal peptide fragment modified with the immobilized compound A and the other peptide fragments are obtained;
in the separation step the other peptide fragments are eluted to selectively collect the N-terminal peptide fragment;
in the cleaving step the disulfide bond in the N-terminal peptide fragment is cleaved to obtain the derivatized N-terminal peptide fragment as sulfonic acid derivative.

Described in (11) and (12) below is an embodiment wherein the biotinylated compound A is used.

(11) The method according to any one of above (1) to (8), wherein in the modification step firstly a biotinylated compound A comprising the compound A further bound to a biotinyl group is prepared; and subsequently the biotinylated compound A is reacted with the N-terminus in the protein or peptide to obtain the protein or peptide modified with the biotinylated compound A at the N-terminus.

(12) The method according to above (8), wherein
in the modification step firstly a biotinylated compound A comprising the compound A further bound to a biotinyl group is prepared, and subsequently the biotinylated compound A is reacted with the N-terminus in the protein or peptide to obtain the protein or peptide modified with the biotinylated compound A at the N-terminus;
in the fragmentation step the N-terminal peptide fragment modified with the biotinylated compound A and the other peptide fragments are obtained;
in the separation step the N-terminal peptide fragment is allowed to adsorb onto an avidin-bound solid support and the other peptide fragments are eluted to selectively collect the N-terminal peptide fragment;
in the cleaving step the disulfide bond in the N-terminal peptide fragment is cleaved to obtain the derivatized N-terminal peptide fragment as sulfonic acid derivative.

2. The invention according to (13) below concerns a method for determining amino acid sequences of proteins or peptides.

(13) A method for analyzing the amino acid sequence of a protein or peptide, wherein the sulfonic acid derivative of a protein or a peptide obtained by the method according to any one of above (1) to (12) is subjected to mass spectrometry.

3. The invention according to (14) through (16) below concerns modified proteins or peptides.

(14) A protein or peptide modified with a disulfide group-containing group at the N-terminus.

(15) The protein or peptide according to above (14), wherein the disulfide group-containing group is further bound to a solid support.

(16) The protein or peptide according to above (14), wherein the disulfide group-containing group is further bound to a biotinyl group.

DETAILED DESCRIPTION OF THE INVENTION

Figure 1:
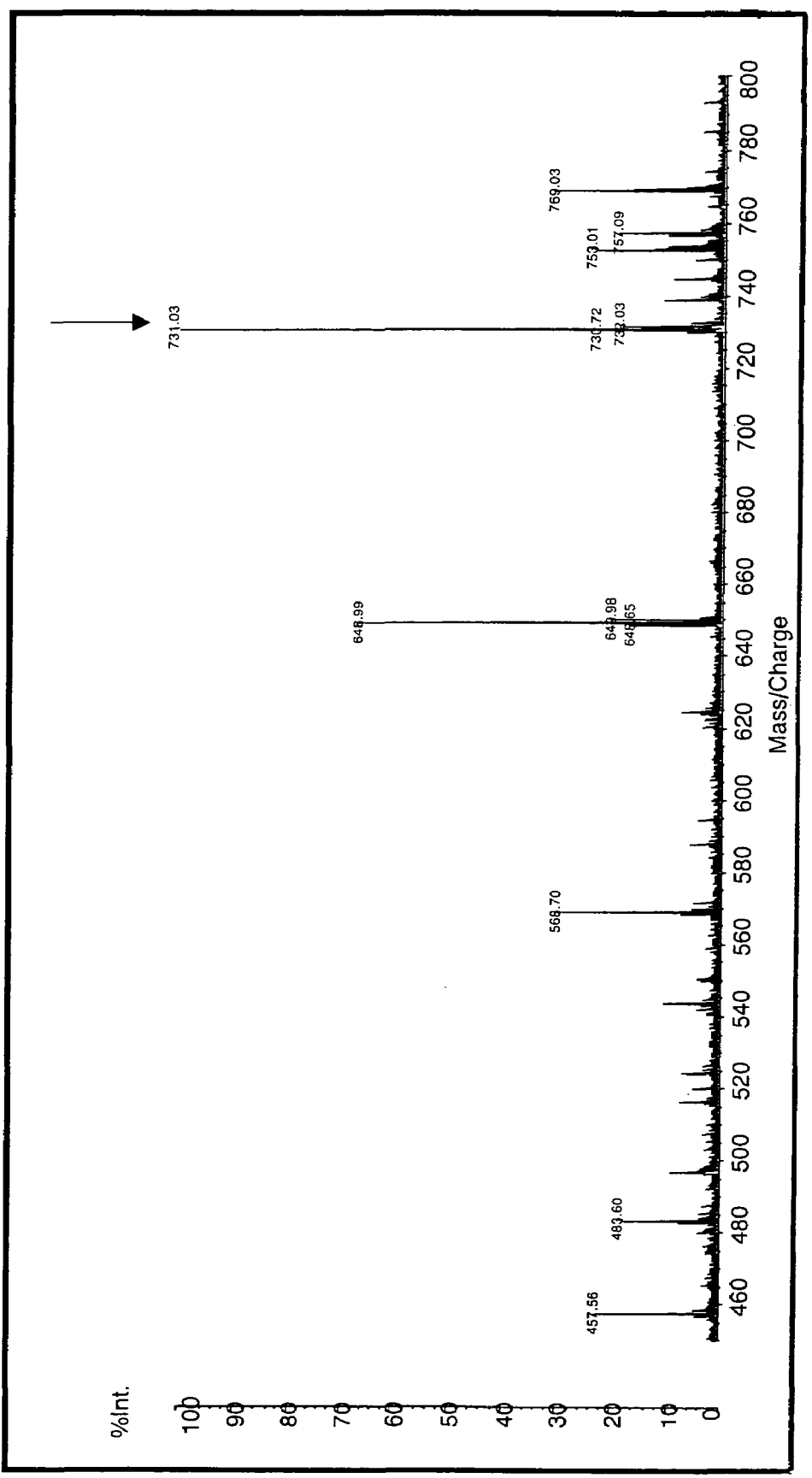
FIG. 1 is a MALDI-TOF MS spectrum obtained in Example 1 of the present invention.

A first aspect of the present invention concerns a method for derivatizing proteins or peptides with sulfonic acid groups at the N-terminus. The method includes a modification step of modifying a protein or a peptide with a compound which has disulfide group (referred to as a compound A) at the N-terminus, and a cleavage step of cleaving the disulfide group into a sulfonic acid group. The method may optionally include a protection step before the modification step and may further include a fragmentation step and a separation step between the modification step and the cleavage step.

[Protection Step]

In the protection step, which may be carried out before the modification step of the method of the present invention, a protein or peptide to be derivatized as sulfonic acid derivative is protected on the side-chain amino groups of amino group-containing amino acid residues. Examples of the amino group-containing amino acid residues include a lysine residue, which includes an $\epsilon$-amino group, and an ornithine residue, which includes a $\delta$-amino group. In the protection step, any reaction can be employed that selectively involves the side-chain amino groups without involving the N-terminal amino groups of a protein or peptide. For example, the guanidination process may preferably be employed to protect the amino groups with guanidino groups. For example, the guanidination process converts lysine residues into homoarginine residues and ornithine residues into arginine residues. Through this step, proteins or peptides protected on the side-chain amino groups are obtained.

In the following, one example of the protection step is described in which a model peptide containing lysine as the only amino group-containing amino acid residue is protected by the guanidination. This process is shown in the following scheme 1:

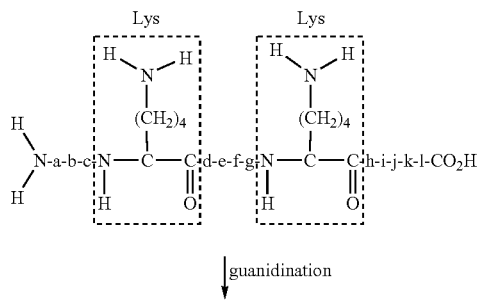

-continued

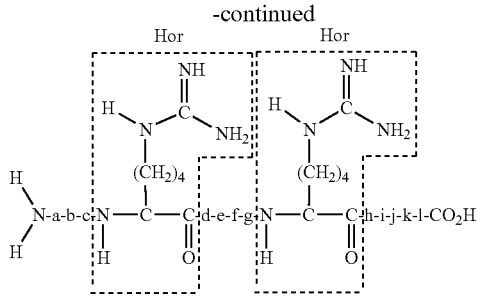

where the letters a through l each indicate an amino acid residue with no side-chain amino groups.

As shown in the scheme 1, the guanidination process converts the side chain-amino groups (—NH$_2$) into guanidino groups (—NHC(=NH)NH$_2$). O-methyl urea, S-methylisothiourea, and 1-guanyl-3,5-dimethylpyrazole are some of the preferred guanidination reagents. In practice, the process is carried out by mixing a protein of interest and a guanidination reagent with a basic solution such as aqueous ammonia. In this manner, proteins or peptides protected by guanidino groups on the side chain-amino groups are obtained.

Since the protection step selectively protects the side chain-amino group and provides no protection to the N-terminal amino acids of proteins or peptides, the N-terminal amino groups can be selectively modified in the subsequent modification step.

[Modification Step]

In the modification step, a protein or a peptide to be derivatized by sulfonic acid groups, or the protected protein or the peptide obtained in the protection step above (which are collectively referred to as "protein or peptide," hereinafter) is modified with a compound A (i.e. disulfide group-containing compound) on the N-terminus.

Specifically, the compound A according to the method of the present invention is a compound that contains a functional group capable of reacting with the N-terminus of a protein or a peptide, and a disulfide group.

A carboxyl group is typically selected as the functional group that can react with the N-terminus of proteins or peptides. Other examples include active group such as isothiocyanate group and active ester group such as succinimidyloxycarbonyl group, p-nitrophenyloxycarbonyl group, pentafluorophenyloxycarbonyl group, tetrafluorosulfophenyloxycarbonyl group. The compound A may further contain a sulfonic acid group, which may be coupled to one of the above functional groups capable of reacting with the N-terminus. The disulfide group should form part of the backbone of the compound A. The example of the compound A include AEDP (3-([2-aminoethyl]dithio)propionic acid hydrochloride), cystine derivatives.

In this step, a protein or a peptide may be reacted with the compound A using a condensation agent in the presence of a base. Examples of the condensation agent used for this purpose include EDC (1-ethyl-3-(3-dimethylaminopropyl)carbodiimide hydrochloride), dicyclohexylcarbodiimide, and diisopropylcarbodiimide. The condensation agent is preferably used for example in an amount of 1 to 50 equivalents of the protein or peptide. Examples of the base include triethylamine, trimethylamine, diisopropylethylamine, and N-ethylmorpholine. The base is preferably used for example in an amount of 1 to 50 equivalents of the protein or peptide. These reagents may be used either independently or in combination of two or more.

Solvents for use in the reaction include dimethylformamide, distilled water, dimethylacetamide, and N-methylpyrrolidone. These solvents may be used either independently or in combination of two or more. Organic solvents may be used at any concentration. The reaction may be carried out at 0 to 70° C. over a time period of 0.1 to 24 hours. The conditions for the reaction can be properly adjusted by any of those skilled in the art.

When the compound A includes the above-described active group as the functional group capable of reacting with the N-terminus of proteins or peptides, the reaction may be carried out without using concentration in an aqueous buffer such as phosphate buffer at 0 to 70° C. over a time period of 0.1 to 24 hours.

In the method of the present invention, the compound A which is immobilized on a solid support (which is referred to as "immobilized compound A," hereinafter) may be used. Such a solid support may be any solid support that includes a functional group capable of binding to part of the backbone of the compound A other than its reaction site with the N-terminus of proteins or peptides. For example, resins containing such functional groups may be used. When AEDP is used as the compound A, isothiocyanate glass beads and the like may be used. In such a case, AEDP are immobilized on the isothiocyanate glass beads by reacting them under basic conditions. In the immobilized compound A, the disulfide group forms part of the backbone.

One example of this step is shown in the following scheme 2, in which AEDP is immobilized on the isothiocyanate glass beads to prepare the immobilized compound A, and the N-terminus of a peptide is modified using the resulting compound A. In the scheme 2, the peptide is protected by guanidination prior to modification. As shown by the scheme 2, the modified peptide is linked to the solid support at the N-terminus via AEDP that serve as a linker.

scheme 2

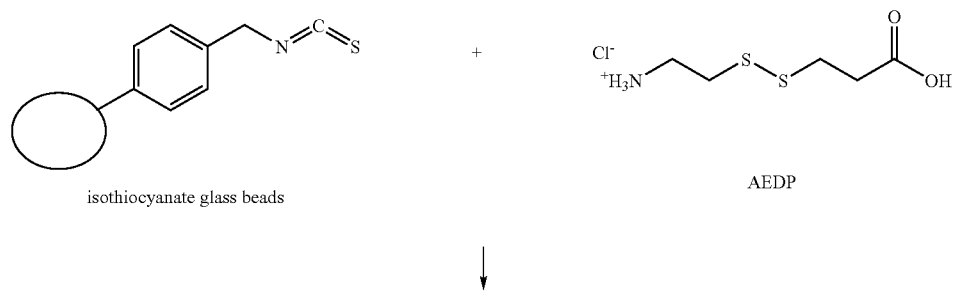

isothiocyanate glass beads

AEDP

↓

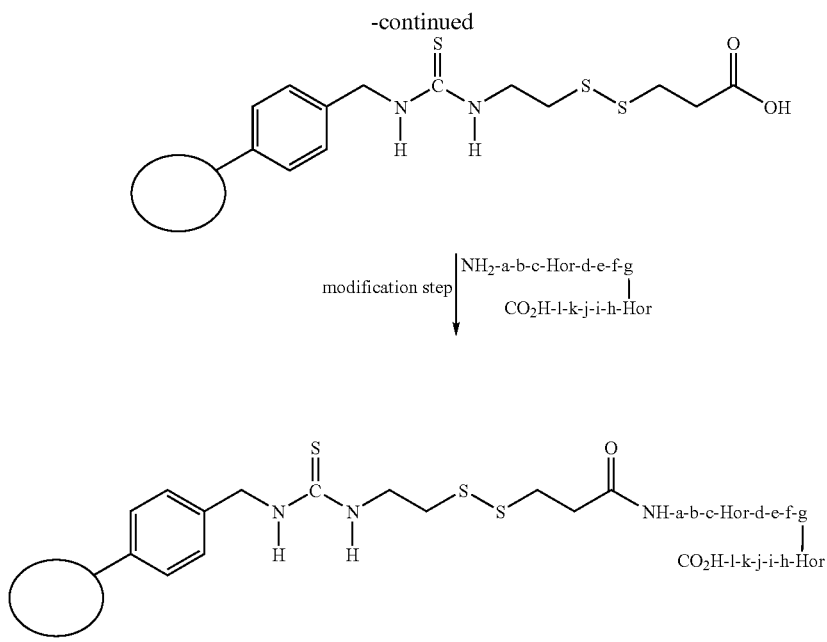

In the method of the present invention, the compound which is bound to a group capable of specifically binding to a solid support may be used. Such a group may be any group that contains both a group capable of binding to part of the backbone of the compound A other than the reaction site with the N-terminus of proteins or peptides and a functional group capable of specifically binding to the solid support. For example, a biotinyl group that can specifically bind to an avidin-bound support and the other group may be used. The compound A which is bound to the biotinyl group (which is referred to as "biotinylated compound A," hereinafter) may be prepared by reacting the compound A with a biotinic acid derivative. In the biotinylated compound A, the disulfide group forms part of the backbone.

Another example of this step is shown in the following scheme 3, in which the N-terminus of a peptide is modified with AEDP bound to the biotinyl group used as the biotinylated compound A. In the scheme 3, the peptide is protected by guanidination prior to modification.

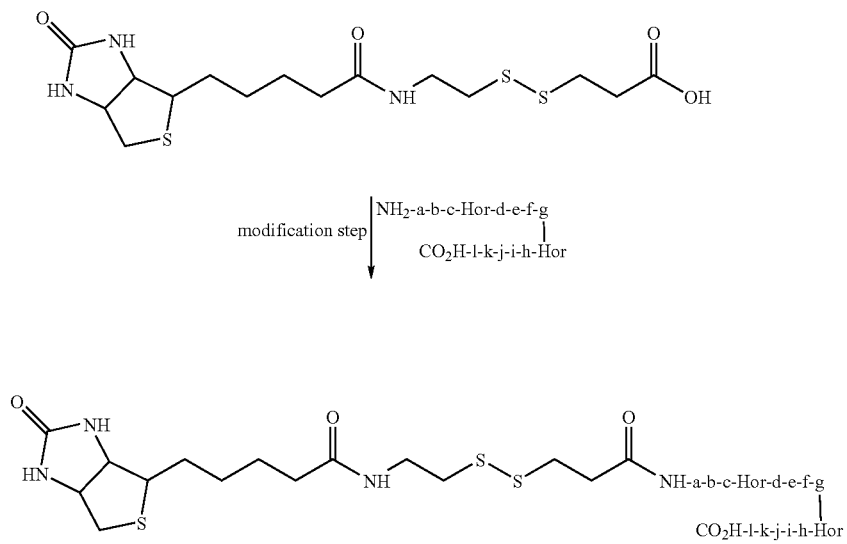

In the manner as described above, a protein or peptide can be modified with the compound A at the N-terminus. The method of the present invention does not require direct introduction of a sulfonic acid derivative at the N-terminus of proteins or peptides as in the conventional method and is thus advantageous in terms of the reaction efficiency at the N-terminus.

[Fragmentation Step and Separation Step]

In the method of the present invention, followed by the modification step, the protein or peptide may be made into fragments (i.e., fragmentation step) prior to the cleavage step, which will be described later. The fragmentation performed in the fragmentation step makes the protein or peptide decomposed into one N-terminal peptide fragments that are derived from the N-terminus of the peptide to be derivatized and one or more of other peptide fragments. The N-termini of the N-terminal peptide fragments contain a disulfide bond derived from the compound A used in the preceding modification step.

The fragmentation may be carried out by chemical fragmentation or enzymatic digestion. Chemical fragmentation may be carried out by using, for example, BrCN. For enzymatic digestion, endoproteases other than Lys-C are used since the guanidinated proteins or peptides do not contain any lysine residues. In the present invention, a suitable enzyme that generates N-terminal peptide fragments with the size readily analyzed by a mass-spectrometer can be selected depending on the protein of interest. For example, trypsin, chymotrypsin, or Glu-C may preferably be used. The enzymatic digestion may be carried out by using known techniques.

Following the fragmentation step, the N-terminal peptide fragments are separated from the other peptide fragments (i.e., Separation step). In the separation step, the N-terminal peptide fragments are selectively collected. Those skilled in the art may readily determine a proper separation technique depending on the nature of the modifying group of the N-terminal peptide fragments.

One example of the fragmentation step and the separation step is shown in the following scheme 4, in which AEDP immobilized on the solid support is used as the immobilized compound A in the preceding modification step:

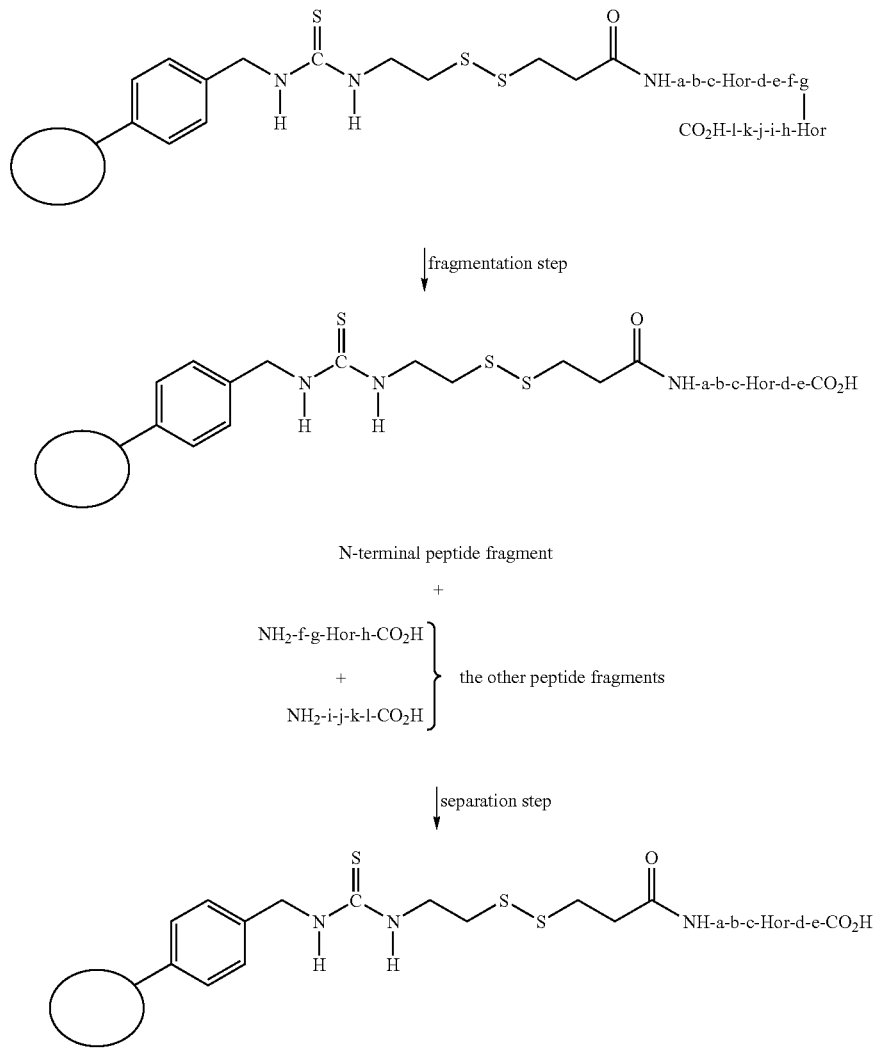

The scheme 4 shows an example in which in the cleavage process an endoprotease that cleaves on the C-terminal side of the residues e and h is used. The fragmentation generates the N-terminal peptide fragments bound to the solid support and the other unbound peptide fragments. The support is then washed in the separation step to remove the other peptide fragments, leaving the N-terminal peptide fragments bound to the support. This allows the collection of the bound N-terminal fragments.

Another example of the fragmentation step and the separation step is shown in the following scheme 5, in which AEDP bound to the biotinyl group is used as the biotinylated compound A in the preceding modification step:

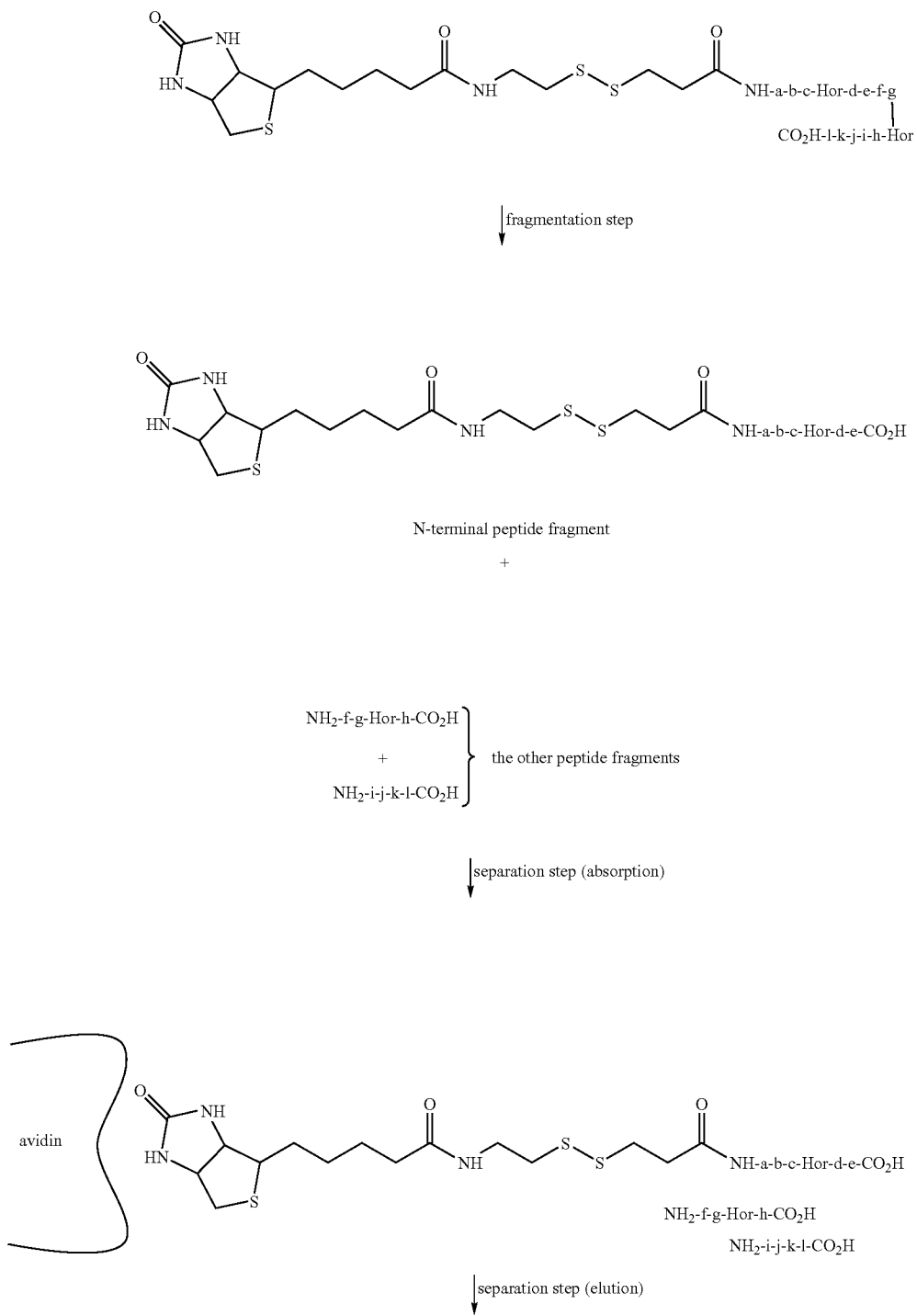

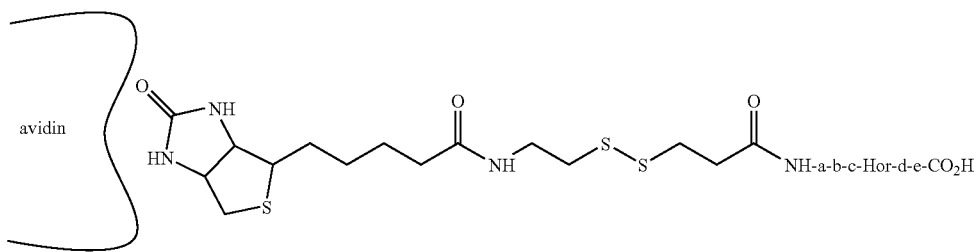

The scheme 5 shows an example in which in the cleavage process an endoprotease that cleaves on the C-terminal side of the residues e and h is used. The fragmentation generates the N-terminal peptide fragments containing biotin and the other non-biotinylated peptide fragments. The mixture of the peptide fragments is then loaded on an avidin column packed with an avidin-bound solid support. As a result, the N-terminal peptide fragments are adsorbed onto the avidin column whereas the other peptide fragments remain free from absorbance onto the column. Subsequently, the avidin column is washed with a phosphate-buffered to elute the other peptide fragments from the column, leaving the N-terminal peptide fragments adsorbed onto the column. This allows the collection of the bound N-terminal fragments.

In this manner, only the N-terminal peptide fragments can be collected. The collected N-terminal peptide fragments are bound to the modifying group derived from the compound A used in the above-described modification step.

[Cleavage Step]

The protein or the peptide obtained in the preceding modification step or the separation step and bound to the modifying group derived from the compound A at the N-terminus is then subjected to the following cleavage step. In this step, the disulfide bond is cleaved, so that the disulfide group is converted into a sulfonic acid group.

The cleavage of the disulfide bond may be carried out either in an oxidative manner or in a reductive manner. The oxidative cleavage may be carried out by a known technique such as the performic acid oxidation technique. The oxidative cleavage converts the sulfide group into a sulfonic acid group. In comparison, reductive cleavage is carried out by first reducing the sulfide group into a thiol group by a known technique using, for example, dithiothreitol and then converting the thiol group into a sulfonic acid group by oxidation with, for example, performic acid.

One example of this step is shown in the following scheme 6, in which AEDP immobilized on the solid support is used as the immobilized compound A in the modification step. As shown in the scheme 6, the cleavage of the disulfide bond generates the N-terminal peptide fragment derivatized as the sulfonic acid derivative:

scheme 6

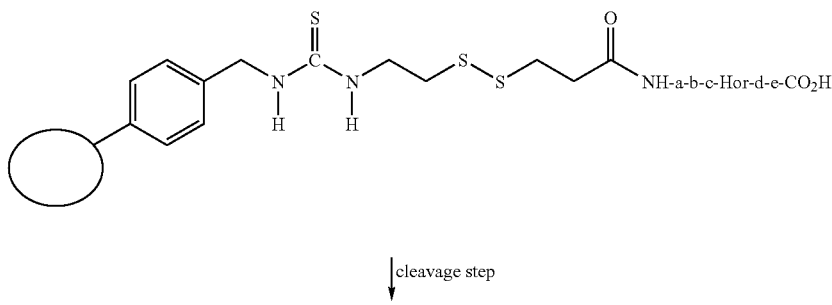

cleavage step

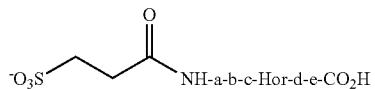

Another example of this step is shown in the following scheme 7, in which AEDP bound to biotinyl group is used as the biotinylated compound A in the modification step. As shown in the scheme 7, the cleavage of the disulfide bond generates the N-terminal peptide fragment derivatized as the sulfonic acid derivative:

scheme 7

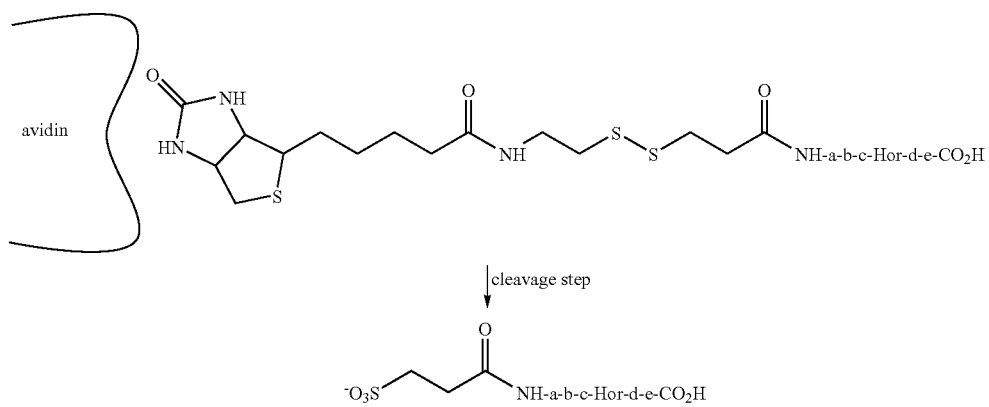

In this manner, derivatives of proteins or peptides introduced with sulfonic acid groups at the N-terminus are obtained. The method of the present invention, in which the N-terminal fragments are collected as a result of the cleavage of disulfide bonds, is more efficient than the methods that rely on, for example, dissociation of avidin-biotin bonds in terms of the recovery of the N-terminal peptide fragments. The sulfonic acid derivatives of proteins or peptides of the present invention can then be subjected to mass spectrometry to determine, for example, the amino acid sequences. During mass spectrometry, the presence of the sulfonic acid groups in the proteins or peptides facilitates the generation of fragment ions.

A second aspect of the present invention is a method for determining the amino acid sequence of proteins or peptides. This method is carried out by preparing the above-described sulfonic acid derivative of the N-terminal peptides as a sample and subjecting the sample to the mass spectrometry. During mass spectrometry, the sulfonic acid groups of the derivatized N-terminal peptides facilitate the generation of fragment ions, simplifying, and increasing the efficiency of, determining amino acid sequence.

A third aspect of the present invention concerns a protein or a peptide modified at the N-terminus with a functional group containing a disulfide group. The disulfide group forms part of the backbone of the compound of the present invention. This compound may be obtained by the processes previously described with reference to the modification step of the method for derivatizing proteins or peptides to sulfonic acid derivatives. The group containing disulfide group in this compound of the present invention is derived from the compound A used in the above modification step. As described in the modification step, examples of the compound A which may be used in the step include the compound immobilized on the solid support and the compound bound to biotinyl group. Therefore, in the compound of the present invention, examples of the group containing disulfide group include a group immobilized on the support, and a group bound to the biotinyl group. Examples of the compound of the present invention are shown in the following structural formulae (I) and (II), where the letters a through l each indicate an amino acid residue and a circle indicates a solid support:

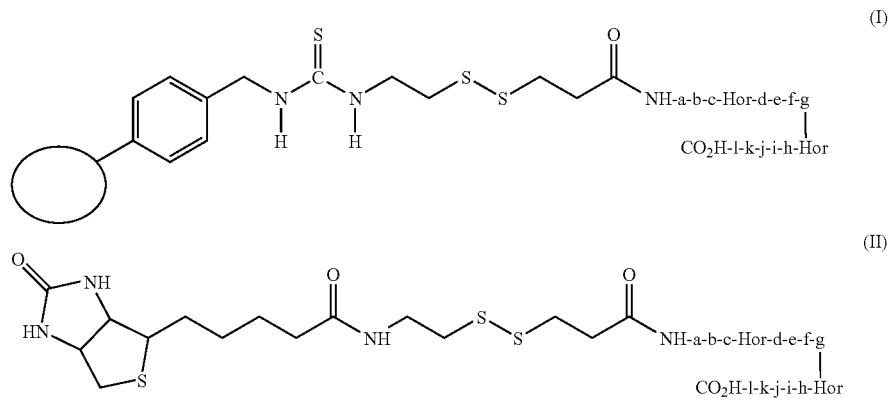

The compound of the present invention is suitable for use as an intermediate for obtaining sulfonic acid derivative in which a sulfonic acid group is introduced at the N-terminal of protein or peptide. The compound of the present invention is easily and efficiently converted into sulfonic acid derivative, by cleavage of the disulfide bond as described in the above cleavage step in the method for derivatizing proteins or peptides to sulfonic acid derivatives.

EXAMPLES

The present invention will now be described in further detail with reference to Examples, which are provided by way of example only and are not intended to limit the scope of the invention in any way. In the following, "%" refers to % by weight unless specifically mentioned. Further, in FIGS. 1 to 4, the horizontal axis corresponds to the Mass/Charge ratio whereas the vertical axis corresponds to the relative intensity of ion peaks (% Int).

Example 1

Preparation of a Support Bound to the Compound A Containing Disulfide Group 10 mg of isothiocyanate glass beads (glass isothiochianate resin) (Sigma) were washed with DMF and were then suspended in 100 µl DMF. To this suspension, 4.6 µmol AEDP (3-([2-aminoethyl]dithio)propionic acid hydrochloride) and 0.5 µl N-methylmorpholine were added and the reaction was allowed to proceed at room temperature for 30 min. Subsequently, the glass beads were washed with DMF and then with distilled water. The resulting support was used in the following modification process.

[Modification of Peptide, Cleavage of Disulfide Bonds, and Mass Spectrometry]

A laminin pentapeptide (Peptide institute) was used as a peptide sample. The laminin pentapeptide used is the amidated form of a peptide that is the cancer-suppressing domain of laminin and has an amino acid sequence of Tyr-Ile-Gly-Ser-Arg-$NH_2$ (SEQ ID NO:1). The sequence is amidated on the C-terminal carboxyl group, and the amidated carboxyl is denoted by adding —$NH_2$.

3 mg of the support prepared above were suspended in 30 µl distilled water. To this suspension, 500 nmol EDC and 500 nmol triethylamine were added and the mixture was left at room temperature for 30 min. Meanwhile, 5 µl (1 nmol/µl) laminin peptapeptide was mixed with 500 nmol triethylamine and the mixture was left at room temperature for 30 min. The two mixtures were then mixed with each other and the reaction was allowed to take place for 30 min. Subsequently, the solid support was washed with distilled water to remove the unreacted reagents. On the other hand, performic acid was prepared by mixing formic acid with a 30 wt % aqueous solution of hydrogen peroxide at a ratio of 19:1 (by volume) and allowing the reaction to proceed at room temperature for 2 hours. 20 µl of the performic acid were added to the solid support and after sealing the reaction vessel, the reaction was allowed to take place at 4° C. for 1 hour. Subsequently, the supernatant was collected and distilled water added, followed by freeze-drying. The sample so obtained was redissolved in a 0.1 w % aqueous solution of trifluoroacetic acid. After desalted using ZipTip C18 (Millipore), the solution was subjected to analysis by MALDI-TOF MS.

Figure 2:
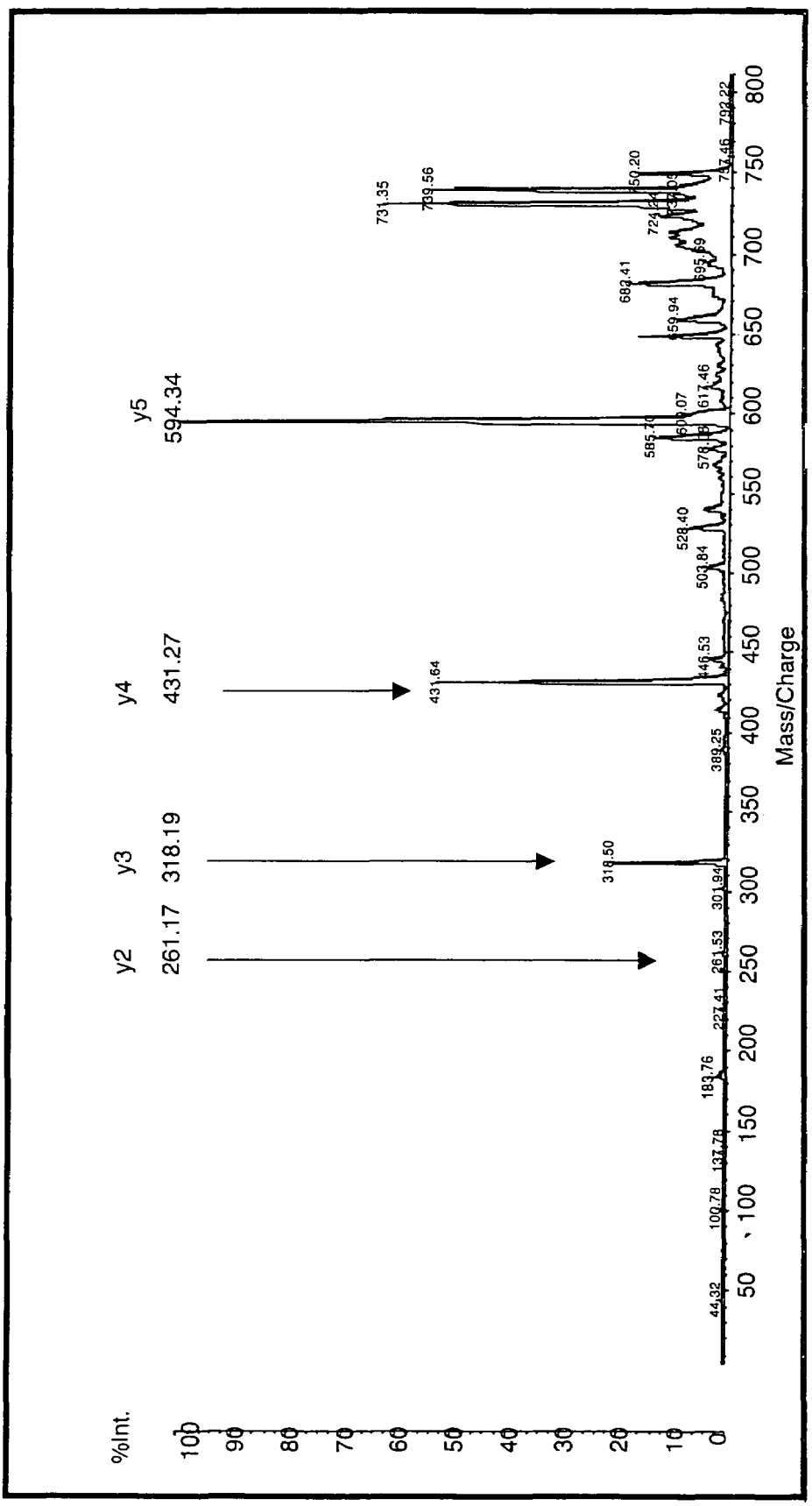
FIG. 2 is a PSD spectrum obtained in Example 1 of the present invention.

FIG. 1 shows a spectrum obtained by MALDI-TOF MS. As shown in FIG. 1, a sulfonic acid derivative of laminin pentapeptide, the desired product, was detected at 731.03 (m/z). FIG. 2 shows a PSD spectrum with the precursor ion at 731.35 (m/z). As shown in FIG. 2, y-series ions containing the C-terminus of the peptide (y2 through y5) were detected and the structure of the peptide was determined from the N-terminus to the fourth residue.

Example 2

This example shows an example in which Lysozyme used as a protein sample is performed reduction-alkylation, N-terminal modification with the disulfide group-containing compound, tryptic digestion, adsorption of the N-terminal peptide fragment using avidin beads, and oxidative cleaving of disulfide bond by performic acid oxidation, and thereby the N-terminal peptide fragment of the Lysozyme is selectively collected as a sulfonic acid derivative.

Lysozyme (EC 3.2.1.17 from Chicken Egg White: SIGMA Chemical Company) is dissolved in distilled water with a concentration of 100 pmol/µl. 10 µl of the resulting dissolved Lysozyme was dropped to PVDF membrane (Polyvinylidene difluoride membrane: Nippon Genetics Co., Ltd.), which was cut to a circular with 8 mm in diameter, and dried to be obtained sample-applied PVDF membrane.

[Reduction-Alkylation]

The protein sample applied PVDF membrane was put into a 1.5 ml plastic tube. 1 ml mixture of 10 mM dithiothreitol in 100 mM ammonium bicarbonate solution and acetonitrile (8:2 v/v) was added to the tube and reacted at 56° C. for 1 hour. After the reaction, the added mixture was removed from the tube. 1 ml mixture of 55 mM iodoacetamide in 100 mM ammonium bicarbonate solution and acetonitrile (8:2 v/v) was added to the tube and reacted with shading at room temperature for 45 minutes. After the reaction, the PVDF membrane was removed from the tube, put into a beaker with 100 ml distilled water, and stirred for 10 minutes to be washed. After the wash, the PVDF membrane was dried.

[Guanidination (Protection of the Side Chain Amino Group)]

The resulting PVDF membrane reduction-alkylation treated was put into a new 1.5 ml tube. 1 ml mixture of 0.85M O-methylisourea hemisulfate (Wako Chemical) in 7N aqueous ammonia and acetonitrile (8:2 v/v) was added to the tube and reacted at 65° C. for 30 minutes. The resulting PVDF membrane is removed from the tube, put into a beaker with 100 ml distilled water, and stirred for 10 minutes to be washed. After the wash, the PVDF membrane was dried.

[N-Terminal Modification of Protein]

The resulting PVDF membrane guanidination treated was put into a new 1.5 ml tube. 100 µl mixture of 10 mM sulfosuccinimidyl-2-(biotinamido)ethyl-1,3-dithiopropionate (Pierce; shown in the following structural formula (III)) in phosphate buffer (pH 7.2), and acetonitrile (8:2 v/v) was added to the tube and reacted at 37° C. for 1 hour. After the reaction, the resulting PVDF membrane was removed from the tube, put into a beaker with 100 ml distilled water, and stirred for 10 minutes to be washed. After the wash, the PVDF membrane was dried.

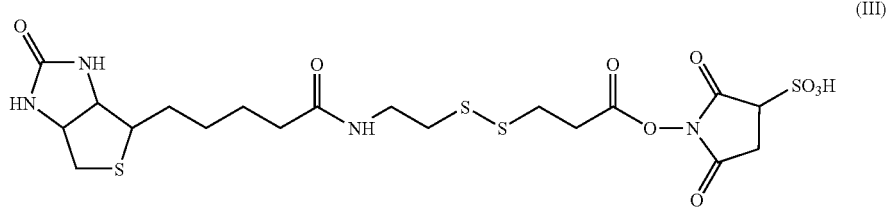

(III)

[tryptic digestion]

The resulting PVDF membrane modification treated was put into a new 1.5 ml tube for digestion. 100 μl mixture of a mixed solution of 1 μg trypsin in 100 mM ammonium bicarbonate and 5 mM calcium chloride solution, and acetonitrile (2:8 v/v) was added to the tube for digestion, and digested at 37° C. overnight.

[Extraction of Digested Peptides from PVDF Membrane]

After the digestion, the liquid part was removed from the tube for digestion to be recovered to a new 1.5 ml tube for recovery. To the PVDF membrane remained in the tube for digestion was added 150 μl mixture of 0.1% aqueous TFA (trifluoroacetic acid) and acetonitrile (4:6 v/v), allowed to stand at 60° C. for 2 hours, to extract digested peptides from the PVDF membrane. The resulting extract solution was recovered to the above mentioned tube for recovery. A series of procedures of extraction of the digested peptides and recovery of the extract solution was done once again. The obtained recovery was dried up using centrifugal concentrator. The resulting dried digested peptides were redissolved in 10 μl of phosphate buffer (pH 7.2).

Figure 3:
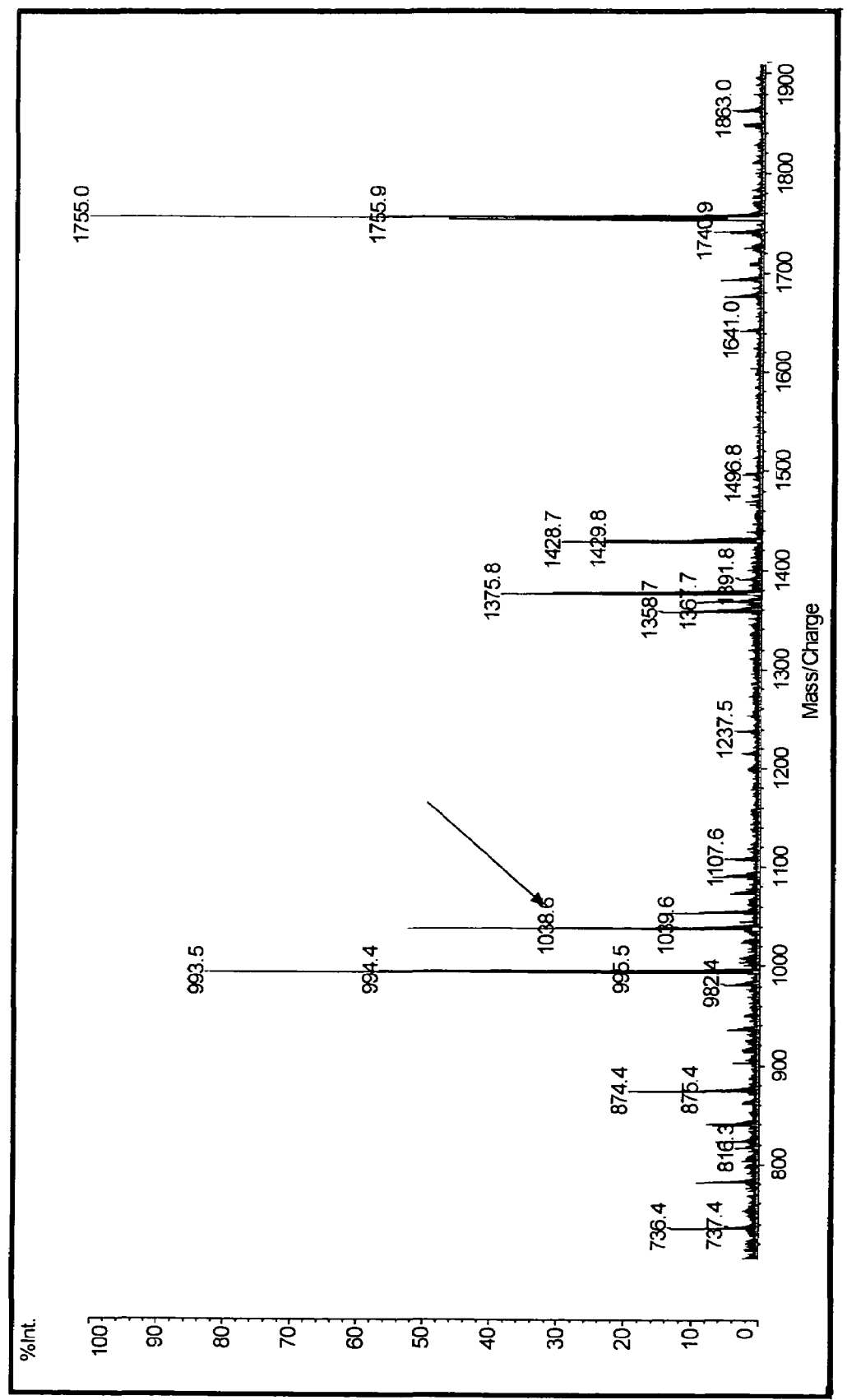
FIG. 3 is a MALDI-TOF MS spectrum obtained for reference in Example 2 of the present invention.

For reference, 2 μl of the resulting redissolved digested peptide is desalted by using ZipTip™ C18(MILLIPORE) and subjected to analysis by MALDI. MALDI spectrum of thus obtained product is shown in FIG. 3, in which the peak marked with an arrow detected at 1037.66 (m/z) corresponds to the N-termianl peptide fragment (Bio-NH(CH$_2$)$_2$—SS—(CH$_2$)$_2$—CO-Hor-Val-Phe-Gly-Arg; SEQ ID NO:2; Bio:biotinyl group, SS:disulfide group, Hor: homoarginine residue), which is guanidinated at lysine residue and modified at the N-terminus with Bio-NH(CH$_2$)$_2$—SS—(CH$_2$)$_2$—CO group. Along with this peak of the N-terminal peptide fragment, many of peaks corresponding to the other peptide fragments (i.e. the fragments derived from the internal sequence of Lysozyme, that is reduced, alkylated and guanidinated) are also detected.

[Selective Collection of N-Terminal Peptide Fragment]

(i) Preparation of Avidin Resin

10 μl avidin resin (SoftLink™ SoftLease Avidin Resin: Promega) was put into a new 1.5 ml tube. 500 μl 0.1M phosphate buffer was added to the tube, stirred, centrifuged to be settled, and removed the supernatant. A series of procedures of adding phophate buffer, stirring, centrifuging and removing supernant was done for 3 times to wash and equilibrate the avidin resin.

(ii) Selective Collection and Elution of the N-Terminal Peptide Fragment

Figure 4:
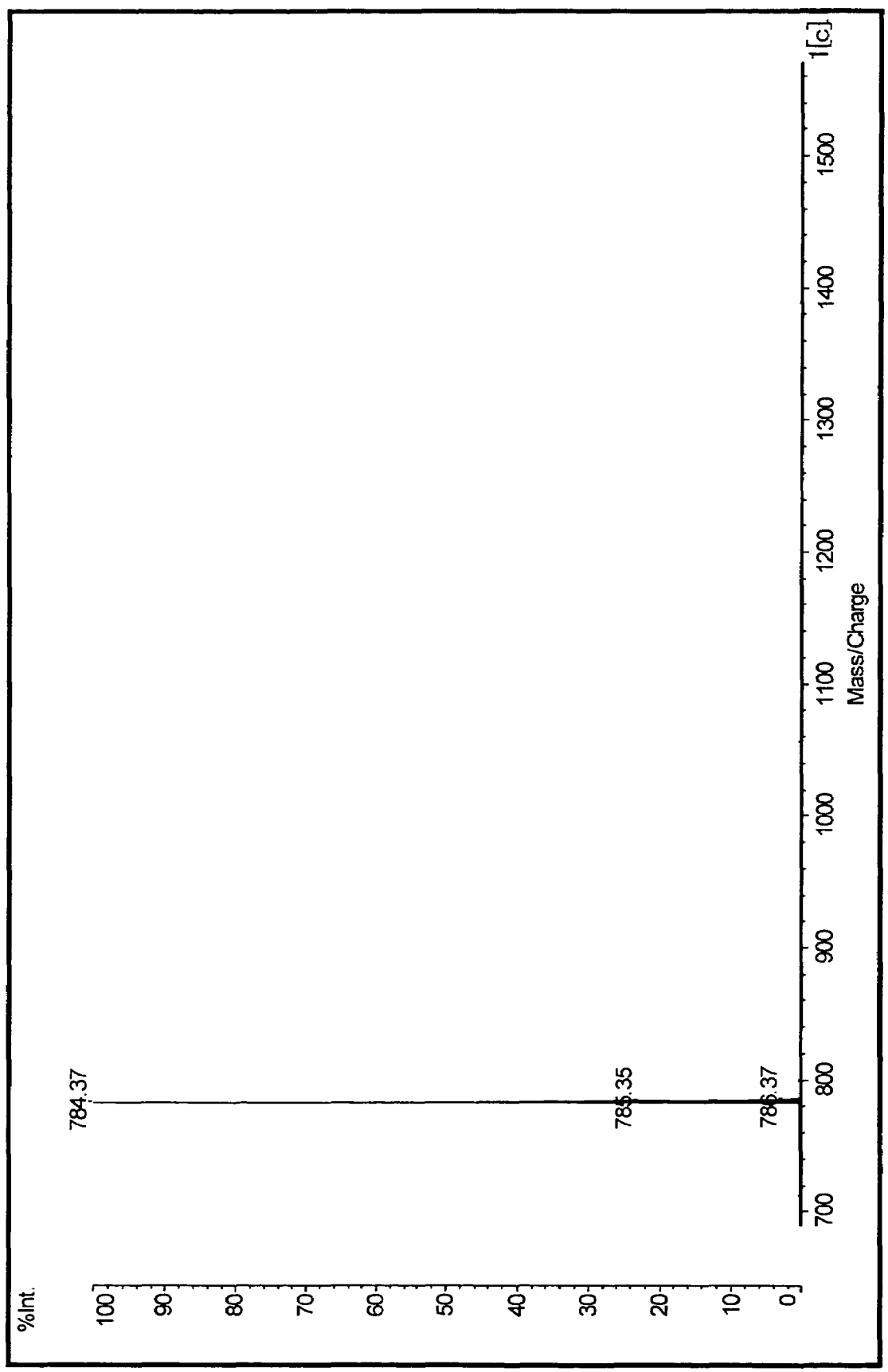
FIG. 4 is a MALDI-TOF MS spectrum obtained in Example 2 of the present invention.

The residual the above redissolved digested peptide was applied to the prepared avidin resin obtained above, and stirred at room temperature for 15 minutes to allow the avidin resin to adsorb the N-terminal peptide fragment. After the adsorption, the avidin resin was washed three times by using 120 μl 0.1M phosphate buffer (pH 7.2) to remove the other peptide than the N-terminal peptide fragment. On the other hand, performic acid was prepared by mixing formic acid with a 30 wt % aqueous solution of hydrogen peroxide at a ratio of 19:1 (v/v) and allowing the reaction to proceed at room temperature for 2 hours. 10 μl of the prepared performic acid were added to the avidin resin, and the reaction was allowed to take place at 4° C. for 1 hour. Subsequently, the supernatant was collected and freeze-dried, to obtain the dried sulfonic acid derivative of N-terminal peptide fragment. The dried sulfonic acid derivative so obtained was redissolved in a 0.1w % aqueous solution of trifluoroacetic acid. After desalted using ZipTip C18 (Millipore), the solution was subjected to analysis by MALDI-TOF MS. MALDI spectrum of thus obtained product is shown in FIG. 4, in which the peak correspond to the sulfonic acid derivative, which is derived from the N-terminal peptide fragment that seen in FIG. 3, is specifically detected at 784.37 (m/z). Accordingly, it has been proven that the N-terminal peptide fragment of Lysozyme was selectively collected as a sulfonic acid derivative.

The above-described Examples shows concrete two modes within the scope of the present invention, however, the present invention can be carried out in various other modes. Therefore, the above-described Examples are merely illustrative in all respects, and must not be construed as being restrictive. Further, the changes that fall within the equivalents of the claims are all within the scope of the present invention.

What is claimed is:

1. A method for derivatizing a protein or peptide to a sulfonic acid derivative, comprising steps of:
    modifying a N-terminus in a protein or peptide with an immobilized compound A bound to a solid support to obtain a protein or peptide modified with the immobilized compound A at the N-terminus, said immobilized compound A comprising a disulfide group and a functional group which reacts with the N-terminus in the protein or peptide;
    fragmenting the obtained protein or peptide modified with the immobilized compound A into a N-terminal peptide fragment comprising the immobilized compound A and containing a disulfide bond, and one or more peptide fragments other than said N-terminal peptide fragment;
    separating the N-terminal peptide fragment from the other peptide fragments to selectively collect the N-terminal peptide fragment; and
    cleaving the disulfide bond of the disulfide group to convert into a sulfonic acid group, thereby converting the modified protein or peptide into a sulfonic acid derivative,
    wherein said immobilized compound A is selected from the group consisting of 3-([2-aminoethyl]dithio)propionic acid hydrochloride (AEDP), cystine, AEDP in which the carboxyl group of AEDP is replaced by an isothiocyanate or active ester, and cystine in which the carboxyl group of cystine is replaced by an isothiocyanate or active ester, and
    wherein in the cleaving step, the disulfide bond in the N-terminal peptide fragment that originates from the immobilized compound A is cleaved and converted into the sulfonic acid group and thereby the derivatized N-terminal peptide fragment is obtained.

2. The method according to claim 1, wherein the conversion to the sulfonic acid group in the cleaving step is carried out by oxidatively cleaving the disulfide bond.

3. The method according to claim 1, wherein the conversion to the sulfonic acid group in the cleaving step is carried out by reductively cleaving the disulfide bond and subsequently an oxidative reaction.

4. The method according to claim 1, further comprising, before the modifying step, protecting the side chain amino group of the protein or peptide.

5. The method according to claim 4, wherein in the protecting step, the side chain amino group is protected by guanidination.

6. The method according to claim 1, wherein
    in the fragmenting step, the N-terminal peptide fragment modified with the immobilized compound A and one or more peptide fragments are obtained;
    in the separating step, the N-terminal peptide fragment is selectively collected after the other peptide fragments are first eluted;
    in the cleaving step, the disulfide bond in the N-terminal peptide fragment is cleaved to obtain the derivatized N-terminal peptide fragment as sulfonic acid derivative.

7. A method for analyzing the amino acid sequence of a protein or peptide, wherein the sulfonic acid derivative of a protein or a peptide obtained by the method according to claim 1 is subjected to mass spectrometry.

8. A method for derivatizing a protein or peptide to a sulfonic acid derivative, comprising steps of:
    modifying a N-terminus in a protein or peptide with a biotinylated compound A to obtain a protein or peptide modified with the biotinylated compound A at the N-terminus, said biotinylated compound A comprising a disulfide group and a functional group which reacts with the N-terminus in the protein or peptide;

fragmenting the protein or peptide modified with the biotinylated compound A into a N-terminal fragment peptide fragment comprising the biotinylated compound A, and one or more peptide fragments other than said N-terminal peptide fragment;

allowing the N-terminal peptide fragment modified with the biotinylated compound A to adsorb onto an avidin-bound solid support;

separating the N-terminal peptide fragment modified with the biotinylated compound A from the other peptide fragments to selectively collect the N-terminal peptide fragment; and cleaving the disulfide bond of the disulfide group in the N-terminal peptide fragment to convert into a sulfonic acid group, thereby converting the modified protein or peptide into a sulfonic acid derivative, wherein said biotinylated compound A is selected from the group consisting of 3-([2-aminoethyl]dithio)propionic acid hydrochloride (AEDP), cystine, AEDP in which the carboxyl group of AEDP is replaced by an isothiocyanate or active ester, and cystine in which the carboxyl group of cystine is replaced by an isothiocyanate or active ester, and wherein in the cleaving step, the disulfide bond in the N-terminal peptide fragment that originates from the biotinylated compound A is cleaved and converted into the sulfonic acid group and thereby the derivatized N-terminal peptide fragment is obtained.

9. The method according to claim 8, wherein the conversion to the sulfonic acid group in the cleaving step is carried out by oxidatively cleaving the disulfide bond.

10. The method according to claim 8, wherein the conversion to the sulfonic acid group in the cleaving step is carried out by reductively cleaving the disulfide bond and subsequently an oxidative reaction.

11. The method according to claim 8, further comprising, before the modifying step, protecting the side chain amino group of the protein or peptide.

12. The method according to claim 11, wherein in the protecting step, the side chain amino group is protected by guanidination.

13. A method for analyzing the amino acid sequence of a protein or peptide, wherein the sulfonic acid derivative of a protein or a peptide obtained by the method according to claim 8 is subjected to mass spectrometry.

14. The method according to claim 1, wherein the active ester group is selected from the group consisting of succinimidyloxycarbonyl group, p-nitrophenyloxycarbonyl group, pentafluorophenyloxycarbonyl group, and tetrafluorosulfophenyloxycarbonyl group.

15. The method according to claim 1, wherein the functional group further comprises a sulfonic acid group.

16. The method according to claim 8, wherein the active ester group is selected from the group consisting of succinimidyloxycarbonyl group, p-nitrophenyloxycarbonyl group, pentafluorophenyloxycarbonyl group, and tetrafluorosulfophenyloxycarbonyl group.

17. The method according to claim 8, wherein the functional group further comprises a sulfonic acid group.

* * * * *